(12) United States Patent
Choi et al.

(10) Patent No.: US 9,408,868 B2
(45) Date of Patent: *Aug. 9, 2016

(54) SKIN EXTERNAL COMPOSITION COMPRISING A COMBINATION OF SODIUM CHLORIDE AND GLUCOSE AS ACTIVE INGREDIENTS FOR TREATING VAGINOSIS AND THE USE THEREOF

(71) Applicant: Won Seog Choi, Jeonju-si, Jeollabuk-Do (KR)

(72) Inventors: Won Seog Choi, Jeonju-si (KR); Dong-Yeul Kwon, Daejeon (KR)

(73) Assignee: Won Seog Choi, Jeonju-si (KR)

(*) Notice: Subject to any disclaimer, the term of this patent is extended or adjusted under 35 U.S.C. 154(b) by 129 days.

This patent is subject to a terminal disclaimer.

(21) Appl. No.: 14/025,654

(22) Filed: Sep. 12, 2013

(65) Prior Publication Data

US 2014/0017340 A1 Jan. 16, 2014

Related U.S. Application Data

(63) Continuation-in-part of application No. 13/501,910, filed as application No. PCT/KR2010/007068 on Oct. 15, 2010, now abandoned.

(30) Foreign Application Priority Data

Oct. 19, 2009 (KR) .................. 10-2009-0099333
Oct. 7, 2010 (KR) .................. 10-2010-0097774

(51) Int. Cl.
| | | |
|---|---|---|
| *A61K 33/14* | (2006.01) | |
| *A61K 47/26* | (2006.01) | |
| *A61K 31/7016* | (2006.01) | |
| *A61K 31/7004* | (2006.01) | |
| *A61K 9/00* | (2006.01) | |

(52) U.S. Cl.
CPC .............. *A61K 33/14* (2013.01); *A61K 9/0034* (2013.01); *A61K 31/7004* (2013.01); *A61K 31/7016* (2013.01); *A61K 47/26* (2013.01)

(58) Field of Classification Search
None
See application file for complete search history.

(56) References Cited

U.S. PATENT DOCUMENTS

| | | | | |
|---|---|---|---|---|
| 2,823,163 | A * | 2/1958 | Thoms | ............... 424/78.1 |
| 2006/0105963 | A1 | 5/2006 | Yang et al. | |
| 2007/0059362 | A1 * | 3/2007 | Rau | ............... 424/466 |
| 2009/0232939 | A1 | 9/2009 | Berge | |

FOREIGN PATENT DOCUMENTS

| | | | | |
|---|---|---|---|---|
| EP | 0628314 | * | 12/1994 | ............ A61K 31/70 |
| KR | 10-2001-0029068 A | | 4/2001 | |

OTHER PUBLICATIONS

Sujatha Srinivasan and David N. Fedricks, Review article, The Human vaginal Bacterial Biota and Bacterial vaginosis, Interdisciplinary Perspectives on Infectious Diseases, vol. 2008, Article ID 750479, p. 1-3.

Choi, J.G. et al., Antibactrerial activity of Ecklonia cava against methicillin-resistant *Staphylococcus aureus* and *Salmonella* spp., Foodborne Pathog. Dis., Apr. 2010; 7(4), pp. 435-441.

Choi, J.G. et al., Antibactrerial activity of Hy;omecon hylomeconoides against methicillin-resistant *Staphylococcus aureus* and *Salmonella* spp., Appl. Biochem. Biotechnol., Apr. 2010; 160(8), pp. 2467-2474.

Seokyung Hahn et al., Reduced osmolarity oral rehydration solution for treatng dehydration due to diarrhea in children:systemic review. British Medical Journal. 323"81-85 (2001).

* cited by examiner

*Primary Examiner* — Rachael E Bredefeld
(74) *Attorney, Agent, or Firm* — Kirk Hahn

(57) ABSTRACT

The present invention relates to a skin external composition comprising a combination of salt and sugar as an active ingredient in an amount effective to treat and prevent vaginosis, together with a pharmaceutically acceptable carrier, and the use thereof.

12 Claims, No Drawings

SKIN EXTERNAL COMPOSITION COMPRISING A COMBINATION OF SODIUM CHLORIDE AND GLUCOSE AS ACTIVE INGREDIENTS FOR TREATING VAGINOSIS AND THE USE THEREOF

CROSS-REFERENCE TO RELATED APPLICATION

The application is a continuation in part application of the US national stage patent application Ser. No. 13/501,910, filed on Apr. 13, 2012.

TECHNICAL FIELD

The present invention relates to a skin external composition comprising a salt and sugar as active ingredients for preventing and treating vaginosis and the use thereof.

BACKGROUND ART

Vaginitis is a condition that occurs especially during pregnancy in the vagina causing vaginal discharge, inflammation, and irritation, as well as vulvar or vaginal itching. The three most common vaginal infections and diseases are also the most frequent causes of vaginitis. The three common vaginal infections include: bacterial vaginosis, vaginal yeast infection, and trichomoniasis.

The human vagina is colonized with various microbes, yeast and germ, for example, about more than $10^4$ numbers/ml (vaginal fluid) of Lactobacillus spp such as Lactobacillus crispatus and Lactobacillus jensenii, which provide weak acidic environment ranging from pH 4.5-5.1 to protect from microbial infection and is a highly versatile organ that can profoundly affect the health of women and their newborn infants. There have been reported that there are many important pathogens in the vaginal niche such as Neiserria gonorrhea, Ureaplasma species, Mycoplasma genitalium, Streptococcus species, Escherichia coli, Chlamydia trachomatis, and Trichomonas vaginalis etc.

Especially, bacterial vaginosis (BV), the most prevalent and detrimental vaginosis, gives rise to malodorous vaginal discharge or local irritation, of the women with BV and is associated with several more serious adverse outcomes including preterm birth, pelvic inflammatory disease, and acquisition of HIV infection. The women with the condition bacterial vaginosis (BV) have loss of many Lactobacillus species (except L. iners) and acquisition of a variety of anaerobic and facultative bacteria. Gram stains of vaginal fluid from women with BV show loss of Gram-positive rods and their replacement with Gram-negative and Gram-variable cocci and rods. Cultures of vaginal fluid from subjects with BV typically yield Gardnerella vaginalis and a mixture of other bacteria that may include Peptosterptococcus, Mobiluncus, Bacterioides, Prevotella, Porphyromonas, Mobiluncus and Mycoplasma species. (Sujatha srinivasan and David N. Fedricks, Review Article, The Human Vaginal Bacterial Biota and Bacterial Vaginosis, Interdisciplinary Perspectives on Infectious Diseases, Vol., 2008, Article ID 750479, p 1-3).

There have been studied to develop effective therapies to treat vaginitis, for example, orally administrated broad spectrum antibiotics such as metronidazole till now. However the therapy shows lots of disadvantages such as antibiotics intolerance, systemic toxicity in case of long-term administration, and a probable destruction of normal bacterial flora in vagina causing to secondary complication such as a decreased number of lactobacillus spp., an increase of vaginal pH, and a proliferation of anaerobic microbes etc.

Accordingly, there has been needed to develop novel therapeutic composition showing long-term treating activity with safety to treat vaginosis.

However, there has been not reported or disclosed on the therapeutic effect for vaginosis of the combination of salt and sugar in any of the above cited literatures, the disclosures of which are incorporated herein by reference.

To investigate an inhibitory effect of the combination of salt and sugar on vaginosis, the inventors of the present invention have carried out antibacterial test, especially Gardnerella vaginalis, a main cause of vaginosis, and finally completed present invention by confirming that the combination showed potent antibacterial activity in the test.

These and other objects of the present invention will become apparent from the detailed disclosure of the present invention provided hereinafter.

SUMMARY OF THE INVENTION

Accordingly, it is another object of the present invention to provide a skin external composition comprising a combination of salt and sugar as an active ingredient in an amount effective to treat or prevent vaginosis, together with a pharmaceutically acceptable carrier.

It is another object of the present invention to provide a use of a combination of salt and sugar in the manufacture of a medicament employed for treating or preventing vaginosis in a mammal.

It is the other object of the present invention to provide a method of treating or preventing vaginosis in a mammal wherein method comprises administering to said mammal an effective amount of a combination of salt and sugar, together with a pharmaceutically acceptable carrier thereof.

DISCLOSURE OF THE INVENTION

In one embodiment of the present invention, the present invention provides a skin external composition comprising a combination of salt and sugar as an active ingredient in an amount effective to treat or prevent vaginosis, together with a pharmaceutically acceptable carrier.

Additionally, the present invention provides a use of a combination of salt and sugar in the manufacture of a medicament employed for treating or preventing vaginosis in a mammal.

Additionally, the present invention provides a method of treating or preventing vaginosis in a mammal wherein method comprises administering to said mammal an effective amount of a combination of salt and sugar together with a pharmaceutically acceptable carrier thereof.

The term, "salt' defined herein comprise a natural salt or processed salt originated from Korea and the other countries, preferably, a pure salt or melted salt, more preferably, sodium chloride or the melted salt prepared by melting a natural salt at the temperature ranging from 200 to 2000° C., preferably, from 800 to 1200° C., for the period ranging from 2 hours to 7 days, preferably, 12 hours to 48 hours.

The term, "sugar' defined herein comprise a saccharide compound, preferably, mono-saccharides such as glucose, fructose, mannose, galactose, etc or disaccharides such as lactose, maltose, sugar, etc, more preferably, glucose, more preferably, crystalline glucose.

The term, "a combination of salt and sugar' defined herein comprise a combination of salt and sugar mixed ratio of 1:1-30 (w/w), preferably, 1:1-10 (w/w), more preferably, 1:1-5 (w/w), most preferably, 1:1-3 (w/w).

The term, "vaginosis" defined herein comprise a vaginosis selected from bacterial vaginosis, fungal vaginitis and Tricomonas vaginitis, preferably, bacteria vaginosis, more preferably, bacterial vaginosis caused *Gardnerella vaginalis*.

The composition of the present invention may further contain the other antibiotics, dye, flavor etc in the amount of about 0.1~20% by weight of the above composition based on the total weight of the composition.

Hereinafter, the present invention is described in detail.

An inventive composition comprising the combination of salt and sugar can be prepared in detail by following procedures, For example, the inventive cleansing combination of the present invention can be prepared by follows; a natural salt or processed salt originated from Korea and the other countries is melted at the temperature ranging from 200 to 2000° C., preferably, from 800 to 1200° C., for the period ranging from 2 hours to 7 days, preferably, 12 hours to 48 hours to obtain the melted salt at the $1^{st}$ step; the melted salt is mixed with sugar compound, preferably, mono-saccharides such as glucose, fructose, mannose, galactose, etc or disaccharides such as lactose, maltose, sugar, etc, more preferably, glucose, more preferably, crystalline glucose with mixed ratio of 1:1-30 (w/w), preferably, 1:1-10 (w/w), more preferably, 1:1-5 (w/w), most preferably, 1:1-3 (w/w) to obtain inventive combination; and the combination is dissolve in an appropriate amount of distilled water, buffer, or isotonic solution, if necessary, with an appropriate amount of the other additives such as the other antibiotics, dye, flavor etc to obtain the inventive cleansing composition.

Accordingly, in an another embodiment of the present invention, the present invention provides a method for preparing the inventive cleansing combination comprising the step: of melting a natural salt or processed salt originated from Korea and the other countries at the temperature ranging from 200 to 2000° C., preferably, from 800 to 1200° C., for the period ranging from 2 hours to 7 days, preferably, 12 hours to 48 hours to obtain the melted salt at the $1^{st}$ step; mixing the melted salt with sugar compound, preferably, mono-saccharides such as glucose, fructose, mannose, galactose, etc or disaccharides such as lactose, maltose, sugar, etc, more preferably, glucose, more preferably, crystalline glucose with mixed ratio of 1:1-30 (w/w), preferably, 1:1-10 (w/w), more preferably, 1:1-5 (w/w), most preferably, 1:1-3 (w/w) to obtain inventive combination; and dissolving the combination in an appropriate amount of distilled water, buffer, or isotonic solution, if necessary, with an appropriate amount of the other additives such as the other antibiotics, dye, flavor etc to obtain the inventive cleansing composition.

It have been proved that the inventive composition comprising a combination of salt and sugar prepared by the above-described method showed potent antibacterial activity, especially, *Gardnerella vaginalis*, a main cause of vaginosis, as well as stimulating the reproduction of lactic acid maintaining vagina acidity by way of stimulating the proliferation of *Latobacillus acidophilus*.

Accordingly, inventive skin external composition comprising a combination of salt and sugar prepared by the above-described method for treating or preventing vaginosis, together with a pharmaceutically acceptable carrier.

Additionally, the present invention provides a use of a combination of salt and sugar prepared by the above-described method in the manufacture of a medicament employed for treating or preventing vaginosis disease in a mammal.

Additionally, the present invention provides a method of treating or preventing vaginosis disease in a mammal wherein method comprises administering to said mammal an effective amount of a combination of salt and sugar prepared by the above-described method, together with a pharmaceutically acceptable carrier thereof.

The term "prevent" defined herein means the inhibition of such those diseases in a mammal which is prone to be caught by those disease and the term "treat" used herein means (a) the inhibition of the development of disease or illness; (b) the alleviation of disease or illness; or (c) the elimination of disease or illness.

The inventive composition may additionally comprise conventional carrier, adjuvants or diluents in accordance with a using method. It is preferable that said carrier is used as appropriate substance according to the usage and application method, but it is not limited. Appropriate diluents are listed in the written text of Remington's Pharmaceutical Science (Mack Publishing co, Easton Pa.).

Hereinafter, the following formulation methods and excipients are merely exemplary and in no way limit the invention.

The composition according to the present invention can be provided as an inventive skin external composition containing pharmaceutically acceptable carriers, adjuvants or diluents, e.g., lactose, dextrose, sucrose, sorbitol, mannitol, xylitol, erythritol, maltitol, starches, acacia rubber, alginate, gelatin, calcium phosphate, calcium silicate, cellulose, methyl cellulose, polyvinyl pyrrolidone, water, methylhydroxy benzoate, propylhydroxy benzoate, talc, magnesium stearate and mineral oil. The formulations may additionally include fillers, anti-agglutinating agents, lubricating agents, wetting agents, flavoring agents, emulsifiers, preservatives and the like. The compositions of the present invention may be formulated so as to provide quick, sustained or delayed release of the active ingredient after their administration to a patient by employing any of the procedures well known in the art.

For example, the compositions of the present invention can be dissolved in distilled water, pH buffer, oils, propylene glycol or other solvents that are commonly used in the art. Suitable examples of the carriers include physiological saline, polyethylene glycol, ethanol, vegetable oils, isopropyl myristate, etc., but are not limited to them. For topical administration, the compounds of the present invention can be formulated in the form of ointments and creams.

The inventive skin external composition of the present invention may be prepared in any form, for example, topical preparation such as cleansing liquid, gel, jelly, foam, cream, ointment, lotion, balm, patch, paste, spray solution, aerosol and the like, or insert preparation such as vaginal tablet, vaginal capsule, vaginal film, vaginal sponge, tampon, pad etc, preferably, vaginal tablet composition or cleansing liquid composition.

Accordingly, the present invention provides a cleansing liquid solution or vaginal tablet composition comprising a combination of salt and sugar for treating or preventing vaginosis, together with a pharmaceutically acceptable carrier.

The composition of the present invention in pharmaceutical dosage forms may be used in the form of their pharmaceutically acceptable salts, and also may be used alone or in appropriate association, as well as in combination with other pharmaceutically active compounds such as antibacterial compounds or extract derived from plant, animal or mineral well-known in the art.

The desirable dose of the inventive extract of the present invention varies depending on the condition and the weight of the subject, severity, drug form, route and period of administration, and may be chosen by those skilled in the art. However, in order to obtain desirable effects, it is generally recommended to administer at the amount ranging 0.001-1000 mg/kg, preferably, 0.01 to 100 mg/kg by weight/day of the combination of the present invention. The dose may be administered in single or divided into several times per day. In terms of composition, the inventive combination should be present between 0.01 to 99.99% by weight, preferably 0.1 to 99%, more preferably, 1 to 20%, most preferably, 5 to 10% by weight based on the total weight of the composition.

The composition of present invention can be administered to a subject animal such as mammals (rat, mouse, domestic animals or human) via various routes. All modes of administration are contemplated, for example, administration can be made externally, topically, orally, rectally or by intravenous, intramuscular, subcutaneous, intracutaneous, intrathecal, epidural or intracerebroventricular injection, preferably, externally or topically.

It will be apparent to those skilled in the art that various modifications and variations can be made in the compositions, use and preparations of the present invention without departing from the spirit or scope of the invention.

BEST MODE FOR CARRYING OUT THE INVENTION

The following Example and Experimental Examples are intended to further illustrate the present invention without limiting its scope.

Example 1

Preparation of an Inventive Combination 1-1. Preparation of Melted Salt 900 mg of natural salt (shinan, Korea), was melted for 24 hours at 850-1000° C. using by heater (MS-E104, TOPS Co. Ltd.) to obtain 400 mg of the melted salt.

1-2. Preparation of Pure Salt 400 mg of pure salt (NaCl, F.W. 58.44) was procured the company (SPPO-91701, Duksan company, Korea).

1-3. Preparation of Glucose 800 mg of glucose (crystalline glucose) was procured the company (Samyang genex Corp., Korea).

1-4. Preparation of Combination (1)

400 mg of the melted salt and 800 mg of glucose prepared in the above steps, were thoroughly mixed together to obtain 1200 mg of the inventive combination (designated as "SG1" hereinafter).

1-5. Preparation of Combination (2)

400 mg of the pure salt (sodium chloride) and 800 mg of glucose prepared in the above steps, were thoroughly mixed together to obtain 1200 mg of the inventive combination (designated as "SG4" hereinafter).

The combinations were kept at −75° C. in refrigerator and used in following experiments by dissolving in distilled water before use.

Example 2

Preparation of Inventive Vaginal Tablet Composition

The combination prepared in Example 1 comprising 400 mg of melted salt and 800 mg of glucose was mixed with 2 mg of magnesium stearate in order to formulating into inventive vaginal tablet composition combination (designated as "SG2" hereinafter) using by entableting apparatus (KT2000, Kumsungkigong).

Example 3

Preparation of Inventive Vaginal Cleansing Solution Composition

The vaginal cleansing solution composition comprising the combination prepared in Example 1 comprising 400 mg of pure salt and 800 mg of glucose was prepared by mixing with following ingredients as shown in Table 1 (designated as "SG3" hereinafter) for 48 hours with stirring.

TABLE 1

| Sg3 solution (100 ml) | | |
|---|---|---|
| Ingredient | | Amount |
| SG4 | | 0.5 g |
| Lactic acid | | 1 g |
| adjuvant | Whey | 180 mg |
| | Ethanol | 1 g |
| | Preservatives (benzalkonimum HCl and menthol) | Trace amount |
| Distilled water | Appropriate amount to adjusted to 100 ml | |

Reference Example 1

Preparation & Reagent 1-1. Experimental Strains

For following test, two strains, (1) *Lactobacillus acidophilus* strain (KRIBB deposit No. KCTC 1120) and (2) *Gadnerella vaginalis* strain (KRIBB deposit No. KCTC 5096) were procured from KCTC (Korean Collection for Type Culture in KRIBB (Korea research Institute of Bioscience & Biotechnology) and cultured in liquid medium (thioglycollate Medium, DIFCO™) at 37° C. or solid medium (blood agar plate) at 37° C. according to anaerobic pouch method (GasPak™, EZ Pouch System).

1-2. Materials

Inventive combination (SG1) prepared in Example 1 was used as a test sample and lactic acid (Fluka Co., ACS reagent, 85-90%, L-lactic acid in water) was used in the experiment.

Experimental Example 1

Effect on the Growth of *Lactobacillus acidophilus*

To test the effect of inventive combination prepared in Example 1 on the growth of *Lactobacillus acidophilus*, following test was performed according to the procedure disclosed in the literature (Choi, J. G. et al, Antibacterial activity of *Ecklonia cava* against methicillin-resitant *Staphylococcus aureus* and *Salmonella* spp., Foodborne Pathog. Dis., 2010 (April): 7(4), pp 435-441).

*Lactobacillus acidophilus* strain (KRIBB deposit No. KCTC 1120) inoculated into fresh blood agar plate was added and cultured in liquid medium (thioglycollate Medium, DIFCO™) at 37° C. in the concentration of $10^5$/ml and various concentrations of the test sample, i.e., 0 mg/ml(negative control), 0.001 mg/ml, 0.1 mg/ml and 10 mg/ml of SG1 and SG4 were treated thereto. The optical density (OD) value was determined using by photometer (Densimat, 50015-PONTE A EMA (F1); Biomerieux Italia S.P.A) in order to check the growth of the stain at 4, 8, 12 and 24 hours after the treatment.

At the result, as can be seen in Table 2, the test sample group treated with inventive combination SG1 and SG4 showed increasing effect on the reproduction of lactic acid maintaining the pH of vaginal environment and the growth of *Lactobacillus acidophilus* strain.

TABLE 2

Effect on the growth of *Lactobacillus acidophilus*

| | | O.D. of *Lactobacillus acidophilus* strain | | | |
|---|---|---|---|---|---|
| | Sample conc. | 4 hrs. | 8 hrs. | 12 hrs. | 24 hrs. |
| Control | 0 mg/ml | 0.2 | 0.6 | 1.2 | 3.6 |
| SG1 | 0.001 mg/ml | 0.2 | 0.6 | 1.2 | 3.9 |
| | 0.1 mg/ml | 0.2 | 0.6 | 1.4 | 4.1 |
| | 10 mg/ml | 0.2 | 0.7 | 1.5 | 4.3 |
| SG4 | 0.001 mg/ml | 0.2 | 0.7 | 1.2 | 4.0 |
| | 0.1 mg/ml | 0.2 | 0.8 | 1.5 | 4.2 |
| | 10 mg/ml | 0.2 | 0.8 | 1.6 | 4.4 |

Experimental Example 2

Effect on the Growth of *Gadnerella vaginalis* Strain

To test the effect of inventive combination prepared in Example 1 on the growth of *Gadnerella vaginalis* strain, a main cause of vaginosis, following Disk diffusion test was performed according to the procedure disclosed in the literature (Choi, J. G. et al, Antibacterial activity of *Hylomecon hylomeconoides* against methicillin-resistant *Staphylococcus aureus, Appl. Biochem. Biotechnol.*, 2010 (April): 160(8), pp 2467-2474).

*Gadnerella vaginalis* strain (KRIBB deposit No. KCTC 5096) inoculated into fresh blood agar plate was added and cultured in 6 mm disk treated with 20 microliter of various concentrations of lactic acid, i.e., 0.1 mg/ml, 1 mg/ml, 10 mg/ml, 100 mg/ml and 1,000 mg/ml of SG1 and SG4 for 24 hours. The inhibition distance (mm) of each disk was determined.

Vaginosis occurs by hyper-proliferation of anaerobic microbes caused by decreased growth of *Lactobacillus* spp. Accordingly, the treatment of lactic acid with *Gadnerella vaginalis* strain forms effective inhibition zone in the disk, which is regarded that the reproduction of lactic acid inhibited the growth of *Gadnerella vaginalis* strain, a main cause of vaginosis.

At the result, as can be seen in Table 3, the test sample group treated with inventive combination SG1 and SG4 potently inhibited the growth of *Gadnerella vaginalis* strain in a dose dependent manner. Therefore, the inventive combination SG1 and SG4 can be useful in treating or preventing vaginosis since it showed potent inhibitory effect on the growth of *Gadnerella vaginalis*.

TABLE 3

Effect on the growth of *Gadnerella vaginalis* strain

| Inhibition diameter (mm) | Treatment concentration of lactic acid with disk (microgram/disk) | | | |
|---|---|---|---|---|
| Control | 0 | 0.2 | 2 | 20 |
| SG1 | 7 | 10 | 18 | 25 |
| SG4 | 8 | 12 | 19 | 28 |

Experimental Example 3

Brief Clinical Test (1)

1200 mg of the vaginal tablet composition (SG2) prepared in Example 2 was administrated intra-vaginally once a day for 5 days to 100 volunteers consisting of 35 patients suffering from vaginosis, and 65 normal women ranging from 20 to 50 years who live in Korea and the direct survey on the effect of inventive composition was performed.

The survey result on (A) the inhibition effect on unpleasant scent, (B) feeling of freshness and (C) alleviation effect on skin pruritus was classified into 4 categories, i.e., (1) very satisfied (2) satisfied, (3) common and (4) dissatisfied according to the intensity of each content and the result was shown in Table 4.

TABLE 4

| | Survey result | | | |
|---|---|---|---|---|---|
| Content | Very satisfied | satisfied | Common | Dissatisfied | Sum |
| A | 79 | 15 | 4 | 2 | 100 |
| B | 72 | 14 | 10 | 4 | 100 |
| C | 67 | 18 | 12 | 3 | 100 |

At the result, as can be seen in Table 4, more than 94% persons among the test group treated with inventive combination SG2 were satisfied with (A) the inhibition effect on unpleasant scent, and more than 86% persons among the test group treated with inventive combination SG2 were satisfied with (B) the feeling of freshness.

Furthermore, more than 85% persons among the test group treated with inventive combination SG2 were satisfied with (C) the alleviation effect on skin. Therefore, the inventive combination SG2 can be useful in treating or preventing vaginosis.

Experimental Example 4

Brief Clinical Test (2)

200 ml of the vaginal cleansing composition (SG3) prepared in Example 3 was administrated externally once a day for 5 days to 100 volunteers consisting of 42 patients suffering from vaginosis, and 58 normal women ranging from 20 to 50 years who live in Korea and the difference of vaginal pH between the pH of (A) before and (B) after the treatment with inventive composition was determined using by pH meter (MP-103, www.yuyuinst.co.kr).

TABLE 5

| | pH difference | | | | | | | |
|---|---|---|---|---|---|---|---|---|
| | pH | | | | | | | |
| | <3.5 | 4 | 4.5 | 5 | 5.5 | 6 | >6.5 | Sum |
| A | 0 | 2 | 7 | 9 | 17 | 49 | 16 | 100 |
| B | 4 | 27 | 37 | 21 | 9 | 2 | 0 | 100 |

At the result, as can be seen in Table 5, the vaginal pH of 82% test group before the treatment with inventive composition had reached to more than 5.5 however that of 89% test group after the treatment with inventive composition reached to normal pH range.

Accordingly, it has been proved that the inventive cleansing composition can be SG3 can be useful in decreasing the vaginal pH of the patients suffering with vaginal akalisation.

The invention being thus described, it will be obvious that the same may be varied in many ways. Such variations are not to be regarded as a departure from the spirit and scope of the present invention, and all such modifications as would be obvious to one skilled in the art are intended to be included within the scope of the following claims.

INDUSTRIAL APPLICABILITY

The inventive composition comprising a combination of salt and sugar showed potent antibacterial activity, especially, *Gardnerella vaginalis*, a main cause of vaginosis, as well as stimulating the reproduction of lactic acid maintaining vagina acidity by way of stimulating the proliferation of *Latobacillus acidophilus*. Accordingly, the inventive combination can be useful in treating or preventing vaginosis and useful in decreasing the vaginal pH of the patients suffering with vaginal akalisation.

The invention claimed is:

1. A method of treatment comprising administering to a mammal in need of treatment for a bacterial vaginosis infection a composition, wherein the composition is placed in a vagina of the mammal and the composition comprises:
    sodium chloride and glucose; wherein the sodium chloride and glucose are 20 to 99.99% by weight of the composition and wherein the weight ratio of sodium chloride to glucose is 1:1-1:30, and
    wherein the bacterial vaginosis infection is a *Gardnerella vaginalis* infection.

2. The method according to claim 1, wherein the composition further comprises a liquid selected from the group consisting of distilled water, a buffered solution, an isotonic solution, a physiological saline, an oil, propylene glycol, ethanol and isopropyl myristate.

3. The method according to claim 1, wherein the treatment is selected from the group consisting of alleviation of the *Gardnerella vaginalis* infection and elimination of the *Gardnerella vaginalis* infection.

4. The method according to claim 1, wherein administering to the mammal comprises administering an amount of the composition ranging from 0.001 mg to 1000 mg per kilogram of body weight of the mammal.

5. The method according to claim 4, wherein the amount of the composition ranges from 0.01 mg to 100 mg per kilogram of body weight of the mammal.

6. The method according to claim 1, wherein the composition is administered from once a day to several times per day.

7. The method according to claim 1, wherein the composition is selected from the group consisting of a topical preparation and an insert preparation.

8. The method according to claim 7, wherein the topical preparation is selected from the group consisting of a cleansing liquid, a gel, a jelly, a foam, a cream, an ointment, a lotion, a balm, a patch, a paste, a spray solution and an aerosol.

9. The method according to claim 8 wherein the topical preparation a cleansing liquid.

10. The method according to claim 7, wherein the insert preparation is selected from the group consisting of a tablet, a capsule, a film, a sponge, a tampon, and a pad.

11. The method according to claim 10 wherein the insert preparation is a tablet.

12. The method of claim 1, wherein the composition further comprises a compound selected from the group consisting of an antibiotic, a dye, and flavor at a concentration from 0.1% to 20% by weight of the composition.

* * * * *